US010338035B2

(12) United States Patent
Huang et al.

(10) Patent No.: US 10,338,035 B2
(45) Date of Patent: Jul. 2, 2019

(54) IMAGING METHOD AND DEVICE BASED ON GUIDED WAVE SCATTERING OF OMNI-DIRECTIONAL MAGNETO-ACOUSTIC TRANSDUCERS

(71) Applicants: Nanchang Hangkong University, Nanchang (CN); Tsinghua University, Beijing (CN)

(72) Inventors: Songling Huang, Beijing (CN); Kai Song, Nanchang (CN); Wei Zhao, Beijing (CN); Chao Lu, Nanchang (CN); Yu Zhang, Beijing (CN); Shen Wang, Beijing (CN); Jiarui Dong, Beijing (CN); Zhe Wang, Beijing (CN)

(73) Assignees: NANCHANG HANGKONG UNIVERSITY, Nanchang (CN); TSINGHUA UNIVERSITY, Beijing (CN)

( * ) Notice: Subject to any disclaimer, the term of this patent is extended or adjusted under 35 U.S.C. 154(b) by 99 days.

(21) Appl. No.: 15/831,894

(22) Filed: Dec. 5, 2017

(65) Prior Publication Data
US 2018/0231503 A1    Aug. 16, 2018

(30) Foreign Application Priority Data
Feb. 13, 2017  (CN) .......................... 2017 1 0076689

(51) Int. Cl.
*G01N 29/44*  (2006.01)
*G01N 29/06*  (2006.01)
(Continued)

(52) U.S. Cl.
CPC ....... *G01N 29/2412* (2013.01); *G01N 29/048* (2013.01); *G01N 29/069* (2013.01); (Continued)

(58) Field of Classification Search
CPC .... G01N 29/07; G01N 29/11; G01N 29/4418; G01N 29/048; G01N 29/4427; G01N 29/069; G01N 29/2412
(Continued)

(56) References Cited

U.S. PATENT DOCUMENTS 5,299,458 A * 4/1994 Clark, Jr. ............... G01N 29/07
                                                                73/597
6,535,625 B1 * 3/2003 Chang ...................... A61B 5/05
                                                                382/128

(Continued)

*Primary Examiner* — Jacques M Saint Surin
(74) *Attorney, Agent, or Firm* — Hodgson Russ LLP

(57) ABSTRACT

An imaging method based on guided wave scattering of omni-directional EMATs includes: selecting an $n^{th}$ omni-directional EMAT from N omni-directional EMATs uniformly arranged in a detection region of a metal plate to be detected as an excitation EMAT; selecting m omni-directional EMATs as omni-directionally receiving EMATs to omni-directionally receive an ultrasonic guided wave signal, and calculating a travel time and intensity of the ultrasonic guided wave signal; judging whether the excitation EMAT and the omni-directionally receiving EMATs form a scattering group, if yes, calculating a position of a scattering point; judging whether the position of the scattering point is within a preset scattering region, if yes, determining the position of the scattering point as an effective scattering point; repeating the above steps until all N omni-directional EMATs have excited omni-directional ultrasonic guided waves, and performing curve fitting on all effective scattering points to obtain a defect profile image.

13 Claims, 5 Drawing Sheets

(51) Int. Cl.
  *G01N 29/04* (2006.01)
  *G01N 29/07* (2006.01)
  *G01N 29/11* (2006.01)
  *G01N 29/24* (2006.01)

(52) U.S. Cl.
  CPC ............ *G01N 29/07* (2013.01); *G01N 29/11* (2013.01); *G01N 29/4418* (2013.01); *G01N 29/4427* (2013.01)

(58) Field of Classification Search
  USPC .......................................................... 73/620
  See application file for complete search history.

(56) References Cited

U.S. PATENT DOCUMENTS

| | | | |
|---|---|---|---|
| 8,492,734 B2* | 7/2013 | Yared | A61B 5/0073 250/458.1 |
| 2013/0327148 A1* | 12/2013 | Yan | G01N 29/34 73/628 |
| 2015/0073729 A1* | 3/2015 | Borigo | G01N 29/2412 702/39 |
| 2018/0172641 A1* | 6/2018 | Huang | G01N 29/069 |
| 2018/0231504 A1* | 8/2018 | Huang | G01N 29/4427 |

* cited by examiner

IMAGING METHOD AND DEVICE BASED ON GUIDED WAVE SCATTERING OF OMNI-DIRECTIONAL MAGNETO-ACOUSTIC TRANSDUCERS

CROSS-REFERENCE TO RELATED APPLICATION

This application claims priority to and benefits of Chinese Patent Application Serial No. 201710076689.X, filed with the State Intellectual Property Office of P. R. China on Feb. 13, 2017, the entire content of which is incorporated herein by reference.

FIELD

The present disclosure relates to the field of non-destructive detection, and more particularly to an imaging method and device based on guided wave scattering of omni-directional magneto-acoustic transducers.

BACKGROUND

Generally, in a process for detecting a metal plate member, it is only possible to judge whether a defect is present and to determine its position if it is present in most case. However, it is more important to obtain quantitative information such as a size and a profile shape of the defect of the metal plate member to be used as an important basis for evaluating a health status of a metal plate and guiding the reparation and maintenance of the metal plate.

With the increasingly strict requirements on the safety of the metal plate member, there are needs to determine the profile shape of the defect, to image the defect with high precision, and to visualize a detection result of the defect.

In the related art, an ultrasonic guided wave has the following features: low attenuation, far propagation distance, 100% coverage of the thickness of the metal plate member a sound field, easy adjustment of a guided wave mode, etc., and guided wave detection with omni-directional magneto-acoustic transducers for an area surrounded by a transducer array from multiple angles can provide more abundant and accurate information of the defects for high-precision imaging of the defects.

However, a strong degree of scattering occurs when the guided wave encounter the defects, an influence and effect of scattering takes a dominant position, the scattering effect may generate more artifacts in a defect image re-established by a traditional guided wave imaging method, resulting in blind regions of the detection, which seriously affects location and imaging accuracy of the defects of the metal material member. In addition, the operation is not simple and convenient, and the efficiency is low.

SUMMARY

The present disclosure seeks to solve at least one of the problems that exist in the related art to at least some extent.

Accordingly, a first objective of the present disclosure is to provide an imaging method based on guided wave scattering of omni-directional magneto-acoustic transducers, with the method, it is possible to perform profile imaging on actually complex defects of the metal plate with high precision and high efficiency under convenient operations, and to accurately solve the position of the scattering point with fast calculation speed.

A second objective of the present disclosure is to provide an imaging device based on guided wave scattering of omni-directional magneto-acoustic transducers.

In order to achieve the above objectives, according to an embodiment of a first aspect of the present disclosure, an imaging method based on guided wave scattering of omni-directional magneto-acoustic transducers is provided. The method includes: S1, selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave, where N is a positive integer; S2, selecting m omni-directional magneto-acoustic transducers from the N omni-directional magneto-acoustic transducers as omni-directionally receiving magneto-acoustic transducers to omni-directionally receive an ultrasonic guided wave signal, and calculating a travel time and intensity of the ultrasonic guided wave signal, where m is a positive integer less than or equal to N; S3, judging whether the excitation magneto-acoustic transducer and the omni-directionally receiving magneto-acoustic transducers form a scattering group, if yes, calculating a position of a scattering point according to the travel time and intensity of the ultrasonic guided wave signal, and a position of the scattering group; S4, judging whether the position of the scattering point is within a preset scattering region, if yes, determining the position of the scattering point as an effective scattering point; S5, repeating the steps S1 to S4 until all of the N omni-directional magneto-acoustic transducers have excited omni-directional ultrasonic guided waves, and performing curve fitting on all effective scattering points acquired to obtain a defect profile image of the metal plate to be detected.

With the imaging method based on guided wave scattering of omni-directional magneto-acoustic transducers according to an embodiment of the present disclosure, by selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave and selecting m omni-directional magneto-acoustic transducers as omni-directionally receiving magneto-acoustic transducers to omni-directionally receive an ultrasonic guided wave signal; further calculating a position of a scattering point according to the travel time and intensity of the ultrasonic guided wave signal and a position of the scattering group when judging that the excitation magneto-acoustic transducer and the omni-directionally receiving magneto-acoustic transducers form a scattering group; and determining the position of the scattering point as an effective scattering point when judging that the position of the scattering point is within a preset scattering region; finally performing curve fitting on all effective scattering points acquired to obtain a defect profile image of the metal plate to be detected after all of the N omni-directional magneto-acoustic transducers have excited omni-directional ultrasonic guided waves, it is possible to perform profile imaging on actually complex defects of the metal plate with high precision and high efficiency under convenient operations, and to accurately solve the position of the scattering point with fast calculation speed.

Alternatively, a formula for calculating the intensity $A_R$ of the ultrasonic guided wave signal is:

$$A_R = \frac{1}{L}\sum_{l=1}^{L} |x(l)|^2,$$

where $x(l)$ is the ultrasonic guided wave signal, where $l=1, 2, \ldots, L$, and L is a total number of data points of the ultrasonic guided wave signals.

Alternatively, judging whether the excitation magneto-acoustic transducer and the omni-directionally receiving magneto-acoustic transducers form a scattering group includes: establishing a planar rectangular coordinate system; determining whether $t_r > t_s$, where $t_r$ is the travel time of the ultrasonic guided wave signal, $t_s$ is a theoretical time for which the ultrasonic guided wave signal propagates from a position T of the excitation magneto-acoustic transducer to a position R of the omni-directionally receiving magneto-acoustic transducer along a straight line and is determined according to $$t_s = \frac{|\overrightarrow{TR}|}{v},$$

where v is a propagation velocity of the ultrasonic guided wave signal, and $|\overrightarrow{TR}|$ is a vector length from the position T to the position R in the planar rectangular coordinate system; and if $t_r > t_s$, determining that the excitation magneto-acoustic transducer and the omni-directionally receiving magneto-acoustic transducers form the scattering group.

Alternatively, formulas for calculating the position of the scattering point according to the travel time and intensity of the ultrasonic guided wave signal, and the position of the scattering group are:

$$|\overrightarrow{TP}| + |\overrightarrow{PR}| = v^* t_r; \text{ and}$$

$$A^* \frac{1}{\sqrt{|\overrightarrow{TP}|}} * a_s * \frac{1}{\sqrt{|\overrightarrow{PR}|}} = A_{RS},$$

where T is a position of the excitation magneto-acoustic transducer, R is a position of the omni-directionally receiving magneto-acoustic transducer, P is the position of the scattering point, $|\overrightarrow{TP}|$ is a vector length from the position T to the position P in a planar rectangular coordinate system $|\overrightarrow{PR}|$ is a vector length from the position P to the position R in the planar rectangular coordinate system, $A_{RS}$ is a signal intensity of a scattered wave received at the position R, A is a signal intensity of the omni-directional ultrasonic guided wave, $\alpha_s$ is a scattering attenuation coefficient of the intensity of the ultrasonic guided wave signal when the ultrasonic guided wave signal is scattered; and $$A^* \frac{1}{\sqrt{|\overrightarrow{TR}|}} = A_{RD},$$

where $A_{RD}$ is a signal intensity of a direct-wave received at the position R.

Alternatively, judging whether the position of the scattering point is within a preset scattering region includes: acquiring a theoretical attenuation amplitude $$A_{Thi} = A^* \frac{1}{\sqrt{|\overrightarrow{TR_i}|}}$$

of the omni-directional ultrasonic guided wave; calculating a transmission intensity comparison threshold $A_{Ht} \in N_\delta$ $(\beta^* A_{Thi}) = (\beta^* A_{Thi} - \delta, \beta^* A_{Thi} + \delta)$ of the guided wave according to the theoretical attenuation amplitude of the omni-directional ultrasonic guided wave, where $\beta$ is a simulation transmission coefficient of the guided wave. $N_\delta(\beta^* A_{Thi})$ is a neighborhood centered as $\beta^* A_{Thi}$ and with a radius of $\delta$; acquiring a scattering attenuation coefficient $$a_s = 1 - \frac{1}{K}\sum_{i=1}^{K} \frac{A_{Ri}}{A_{Thi}}$$

of the intensity of the ultrasonic guided wave signal when the ultrasonic guided wave signal is scattered, where a calculating number K is $K = \text{Count}(i)$ s.t. $(A_{Ri} < A_{Ht})$, where Count (i) is a function for counting i; obtaining the preset scattering region according to K positions of the omni-directionally receiving magneto-acoustic transducers and a position of the excitation magneto-acoustic transducer, and judging whether the position of the scattering point is within the preset scattering region.

Alternatively, a formula for the curve fitting is:

$$D(x) = \arg\left(\min\sum_{j=1}^{S} |\phi(x_j) - y_j|^2 \text{ s.t. } \frac{d\phi}{dx}\bigg|_{P_j} = \frac{dy}{dx}\bigg|_{P_j}\right)$$

where S is a total number of the effective scattering points, S is a positive integer, and a position of a $j^{th}$ scattering point is $P_j(x_j, y_j)$ in a planar rectangular coordinate system, where $j=1, 2, \ldots S$.

In order to achieve the above objectives, according to an embodiment of a second aspect of the present disclosure, an imaging device based on guided wave scattering of omni-directional magneto-acoustic transducers is provided. The device includes: a processor; and a memory for storing instructions executable by the processor, in which the processor is configured to perform the imaging method based on guided wave scattering of omni-directional magneto-acoustic transducers according to embodiments of the first aspect of the present disclosure.

In order to achieve the above objectives, according to an embodiment of a third aspect of the present disclosure, there is provided a non-transitory computer-readable storage medium having stored therein instructions that, when executed by a processor of a mobile terminal, causes the mobile terminal to perform the imaging method based on guided wave scattering of omni-directional magneto-acoustic transducers according to embodiments of the first aspect of the present disclosure.

Additional aspects and advantages of embodiments of the present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings as described below.

DETAILED DESCRIPTION

Figure 1:
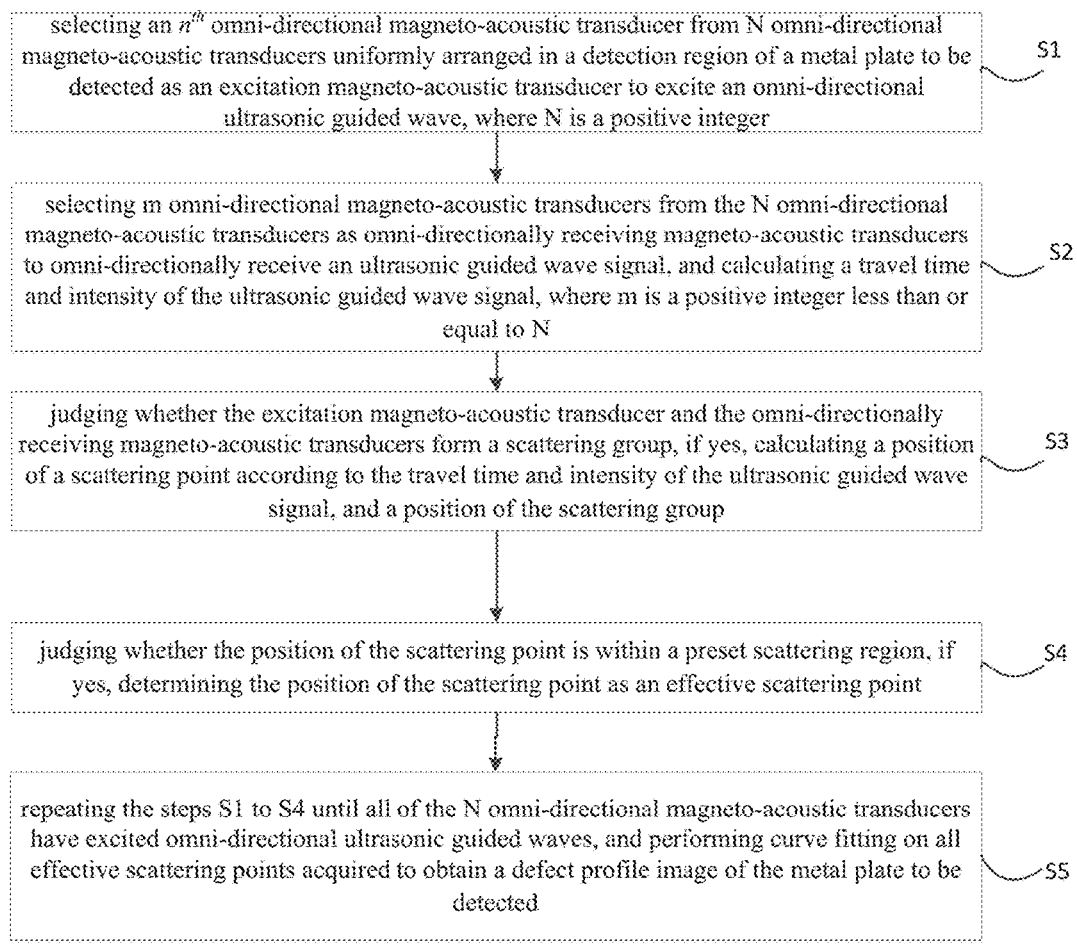
FIG. 1 is a flow chart of an imaging method based on guided wave scattering of omni-directional magneto-acoustic transducers according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

An imaging method and device based on guided wave scattering of omni-directional magneto-acoustic transducers according to embodiments of the present disclosure will be described below with reference to the accompanying drawings.

Generally, in a process for detecting a metal plate member, it is only possible to judge whether a defect is present and to determine its position if it is present in most case. With the increasingly strict requirements on the safety of the metal plate member, the technology for detecting the metal plate member is also developing.

In the related art, guided wave detection with omni-directional magneto-acoustic transducers for an area surrounded by a transducer array from multiple angles can provide more abundant and accurate information of the defects for high-precision imaging of the defects. However, a strong degree of scattering occurs when the guided wave encounter the defects, an influence and effect of scattering takes a dominant position, and the scattering effect may generate more artifacts in a defect image re-established by a traditional guided wave imaging method, resulting in blind regions of the detection, which seriously affects location and imaging accuracy of the defects of the metal material member.

In addition, a shape of an actual defect is very complex, scattering characteristics are varied, and it is difficult to find a unified model to describe the scattering process and extract the scattering characteristics. Moreover, because the transmission and propagation directions of the guided wave do not have a unique certainty, detection based on guided wave scattering of an omni-directional magneto-acoustic transducer makes it different to construct a model for re-establishing a defect profile from a scattering signal of the guided wave.

In order to avoid the above-mentioned problems, an imaging method based on guided wave scattering of omni-directional magneto-acoustic transducers is provided according to an embodiment of the present disclosure. By uniformly arranging the omni-directional magneto-acoustic transducers EMATs around a detection region, using a travel time and intensity of each guided wave signal, and a corresponding position relationship of a scattering group, a model and method are established for solving the position of the scattering point in high-precision, effective scattering points are sieved out, a curve fitting is performed on all of the effective scattering points to establish a clear profile image of the actually complex defect, and the calculation is accurate, efficient and rapid, thus solving the following problems: the imaging precision of the actually complex defects of the metal plate detected with magneto-acoustic ultrasonic guided wave is low, the characteristic of the defect is difficult to extract, and a model for re-establishing the defect profile with the omni-directional transducer is difficult to solve.

FIG. 1 is a flow chart of an imaging method based on guided wave scattering of omni-directional magneto-acoustic transducers according to an embodiment of the present disclosure.

As shown in FIG. 1, the imaging method based on guided wave scattering of omni-directional magneto-acoustic transducers includes the following steps.

Step 1: an $n^{th}$ omni-directional magneto-acoustic transducer is selected from N omni-directional magneto-acoustic transducers uniformly arranged in a detection region of a metal plate to be detected as an excitation magneto-acoustic transducer to excite an omni-directional ultrasonic guided wave, where N is a positive integer.

Specifically, the N omni-directional magneto-acoustic transducers may be arranged in any form as long as they are uniformly arranged in the detection region of the metal plate to be detected. For example, the N omni-directional magneto-acoustic transducers are uniformly arranged in a circular array.

It may be appreciated that each of the omni-directional magneto-acoustic transducers excites an omni-directional ultrasonic guided wave in a certain order in the detection region of the metal plate to be detected, thus, the $n^{th}$ omni-directional magneto-acoustic transducer may be selected as the excitation magneto-acoustic transducer to excite the omni-directional ultrasonic guided wave. It may also be appreciated that each of the omni-directional magneto-acoustic transducers omni-directionally receives the ultrasonic guided wave signal when there is an ultrasonic guided wave in the detection region of the metal plate to be detected. That is, each of the omni-directional magneto-acoustic transducers has dual functions of exciting the omni-directional ultrasonic guided wave and omni-directionally receiving the ultrasonic guided wave signal.

It should be noted that the omni-directional magneto-acoustic transducer mainly consists of a cake-shaped densely packed coil powered by an alternating current, an open-ended nickel ribbon ring top-magnetized in a circumferential direction, and the metal plate to be detected itself below the omni-directional magneto-acoustic transducer.

As a scene implementation, 16 omni-directional magneto-acoustic transducers (EMATs) are uniformly arranged in a circular array around a detection region of a steel plate to be detected. The thickness of the steel plate is 4 mm, the diameter of the omni-directional magneto-acoustic transducer is 35 mm, and the diameter of the circular array is 54 cm. The $1^{st}$ omni-directional magneto-acoustic transducer is selected as the excitation magneto-acoustic transducer to excite the omni-directional ultrasonic guided wave.

Step 2: m omni-directional magneto-acoustic transducers are selected from the N omni-directional magneto-acoustic transducers as omni-directionally receiving magneto-acoustic transducers to omni-directionally receive an ultrasonic guided wave signal, and a travel time and intensity of the ultrasonic guided wave signal are calculated, where m is a positive integer less than or equal to N.

Specifically, when there is an ultrasonic guided wave signal in the metal plate, all or part of the omni-directional magneto-acoustic transducers may omni-directionally receive the ultrasonic guided wave signal.

Specifically, a formula for calculating the intensity $A_R$ of the ultrasonic guided wave signal is:

$$A_R = \frac{1}{L}\sum_{l=1}^{L} |x(l)|^2,$$

where $x(l)$ is the ultrasonic guided wave signal, where $l=1, 2, \ldots, L$, and L is a total number of data points of the ultrasonic guided wave signals.

Description is continued for the scene implementation above, m may be 12.

Step 3: it is judged whether the excitation magneto-acoustic transducer and the omni-directionally receiving magneto-acoustic transducers form a scattering group, if yes, a position of a scattering point is calculated according to the travel time and intensity of the ultrasonic guided wave signal, and a position of the scattering group.

Specifically, judging whether the excitation magneto-acoustic transducer and the omni-directionally receiving magneto-acoustic transducers form a scattering group includes: establishing a planar rectangular coordinate system; determining whether $t_r > t_s$, where $t_r$ is a travel time of a certain ultrasonic guided wave signal, $t_s$ is a theoretical time for which the ultrasonic guided wave signal propagates from a position T of the excitation magneto-acoustic transducer to a position R of the omni-directionally receiving magneto-acoustic transducer along a straight line and is determined according to $$t_s = \frac{|\overrightarrow{TR}|}{v},$$

where v is a propagation velocity of the ultrasonic guided wave signal. e.g., a propagation velocity of an ultrasonic guided wave signal in the metal plate is v=3200 m/s, and $|\overrightarrow{TR}|$ is a vector length from the position T to the position R in the planar rectangular coordinate system, and if $t_r > t_s$, determining that the excitation magneto-acoustic transducer and the omni-directionally receiving magneto-acoustic transducers form the scattering group.

It should be noted that if $t_r > t_s$ is invalid, the excitation magneto-acoustic transducer and the omni-directionally receiving magneto-acoustic transducer do not form a scattering group for the ultrasonic guided wave signal.

It may be appreciated that, for each time, there is only one excitation magneto-acoustic transducer, and several omni-directionally receiving magneto-acoustic transducers, and after determining that the excitation magneto-acoustic transducer and the omni-directionally receiving magneto-acoustic transducer do not form the scattering group, it is needed to judge whether the excitation magneto-acoustic transducer and a next omni-directionally receiving magneto-acoustic transducer form a scattering group.

Specifically, formulas for calculating the position of the scattering point according to the travel time and intensity of the ultrasonic guided wave signal, and the position of the scattering group are:

$$|\overrightarrow{TP}| + |\overrightarrow{PR}| = v^* t_r; \text{ and}$$

$$A^* \frac{1}{\sqrt{|\overrightarrow{TP}|}} * a_s * \frac{1}{\sqrt{|\overrightarrow{PR}|}} = A_{RS},$$

where T is a position of the excitation magneto-acoustic transducer, R is a position of the omni-directionally receiving magneto-acoustic transducer, P is the position of the scattering point, $|\overrightarrow{TP}|$ is a vector length from the position T to the position P in a planar rectangular coordinate system, $|\overrightarrow{PR}|$ is a vector length from the position P to the position R in the planar rectangular coordinate system, $A_{RS}$ is a signal intensity of a scattered wave received at the position R, A is a signal intensity of the omni-directional ultrasonic guided wave, $\alpha_s$ is a scattering attenuation coefficient of the intensity of the ultrasonic guided wave signal when the ultrasonic guided wave signal is scattered; and $$A^* \frac{1}{\sqrt{|\overrightarrow{TR}|}} = A_{RD},$$

where $A_{RD}$ is a signal intensity of a direct-wave received at the position R.

Step 4: it is judged whether the position of the scattering point is within a preset scattering region, if yes, the position of the scattering point is determined as an effective scattering point.

Specifically, judging whether the position of the scattering point is within a preset scattering region includes: acquiring a theoretical attenuation amplitude $$A_{Thi} = A^* \frac{1}{\sqrt{|\overrightarrow{TR_i}|}}$$

of the omni-directional ultrasonic guided wave; calculating a transmission intensity comparison threshold $A_{Hi} \in N_\delta$ $(\beta^* A_{Thi}) = (\beta^* A_{Thi} - \delta, \beta^* A_{Thi} + \delta)$ of the guided wave according to the theoretical attenuation amplitude of the omni-directional ultrasonic guided wave, where $\beta$ is a simulation transmission coefficient of the guided wave, $N_\delta(\beta^* A_{Thi})$ is a neighborhood centered as $\beta^* A_{Thi}$ and with a radius of $\delta$; acquiring a scattering attenuation coefficient $$a_s = 1 - \frac{1}{K}\sum_{i=1}^{K} \frac{A_{Ri}}{A_{Thi}}$$

of the intensity of the ultrasonic guided wave signal when the ultrasonic guided wave signal is scattered, where a calculating number K is K=Count(i) s.t. $(A_{Ri} < A_{Hi})$, where Count (i) is a function for counting i; obtaining the preset scattering region according to K positions of the omni-directionally receiving magneto-acoustic transducers and a position of the excitation magneto-acoustic transducer, and judging whether the position of the scattering point is within the preset scattering region.

It may be appreciated that judging whether the position of the scattering point is within a sector region, if yes, the scattering point is an effective scattering point, and if no, the scattering point is an invalid scattering point and is removed from a set of solved results of the scattering points.

Step 5: the steps S1 to S4 are repeated until all of the N omni-directional magneto-acoustic transducers have excited omni-directional ultrasonic guided waves, and curve fitting is performed on all of the acquired effective scattering points so as to obtain a defect profile image of the metal plate to be detected.

Specifically, a formula for the curve fitting is:

$$D(x) = \arg(\min \sum_{j=1}^{S} |\phi(x_j) - y_j|^2 \text{ s.t. } \frac{d\phi}{dx}|_{P_j} = \frac{dy}{dx}|_{P_j})$$

where S is a total number of the effective scattering points, S is a positive integer, and a position of a $j^{th}$ scattering point is $P_j(x_j, y_j)$ in a planar rectangular coordinate system, where j=1, 2, . . . , S.

The above-described processes and the results of the present disclosure will be more clearly understood by those skilled in the art, with reference to illustrations below in connection with FIGS. 2 and 3.

Figure 2:
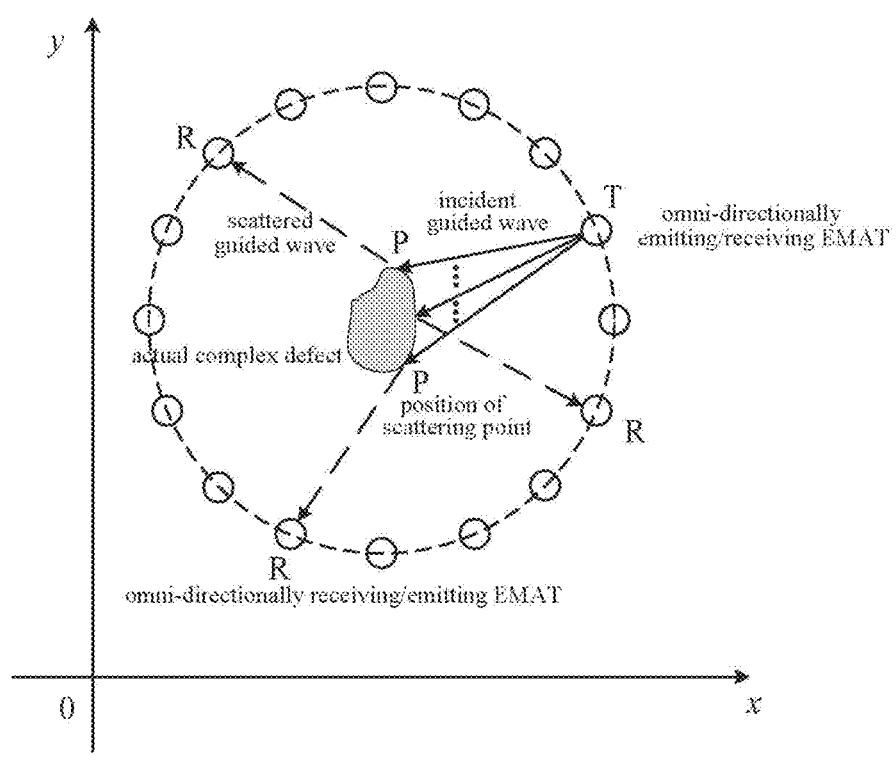
FIG. 2 is a schematic diagram of an experimental structure according to an embodiment of the present disclosure.
Figure 3:
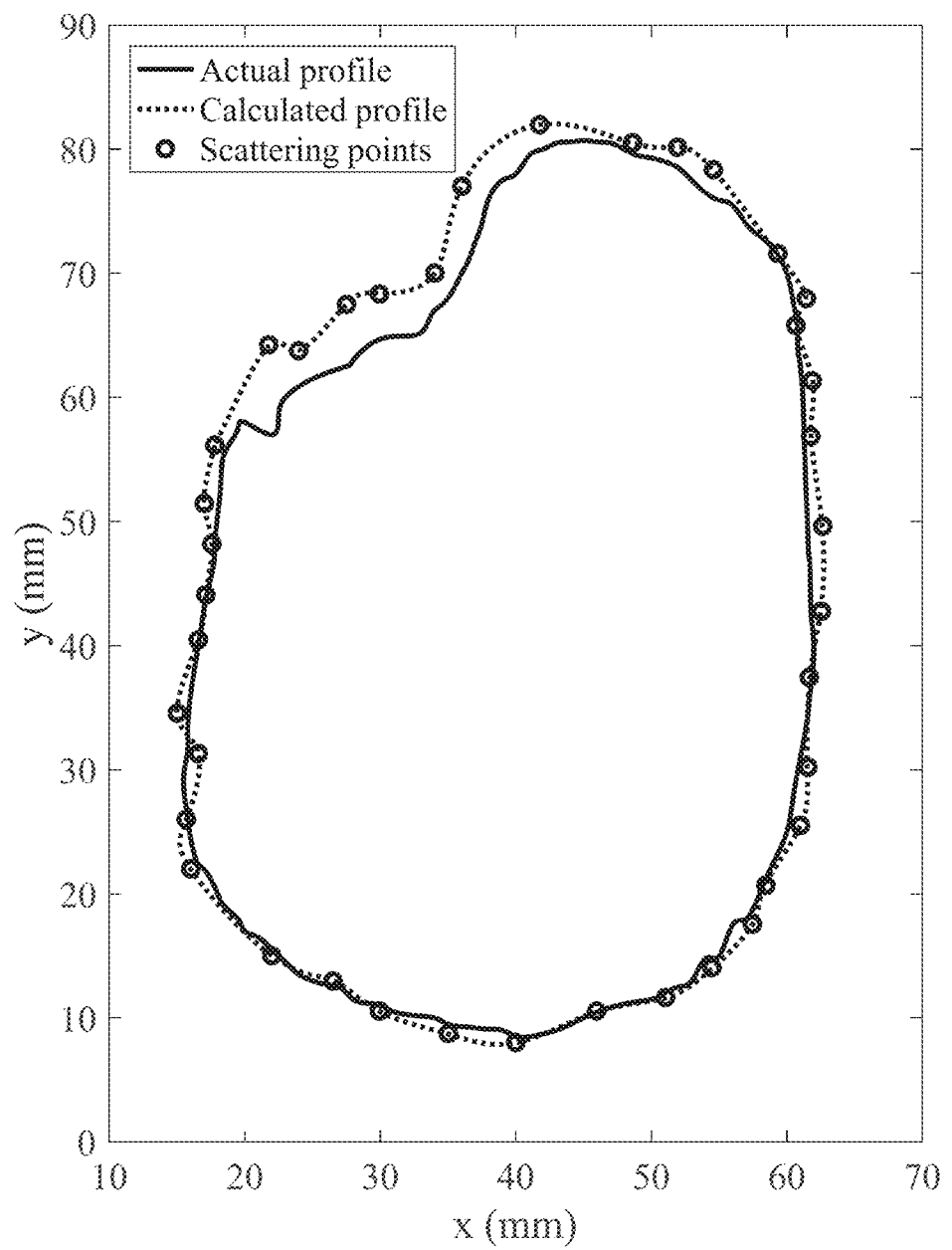
FIG. 3 is a schematic diagram of a result of defect profile imaging of a metal plate according to an embodiment of the present disclosure.

FIG. 2 is a schematic diagram of an experimental structure according to an embodiment of the present disclosure, which can be illustrated in connection with the above embodiments. FIG. 3 is a schematic diagram of a result of a defect profile imaging of a metal plate according to an embodiment of the present disclosure. As shown in FIG. 3, the number of the omni-directional magneto-acoustic transducers is 16, L is 5000, v is 3200 m/s, the simulation transmission coefficient β of the guided wave is 0.9, and 39 scattering points are obtained in total. A fitted curve formed according to the positions of the scattering points and directions of scattering sides is very close to an actual profile of the defect of the steel plate. With the defect profile imaging detection of the metal plate performed by the method of the present disclosure, the imaging accuracy is high, and a clear profile image of the defect may be obtained.

In summary, with the imaging method based on guided wave scattering of omni-directional magneto-acoustic transducers according to an embodiment of the present disclosure, by selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave and selecting m omni-directional magneto-acoustic transducers as omni-directionally receiving magneto-acoustic transducers to omni-directionally receive an ultrasonic guided wave signal; further calculating a position of a scattering point according to the travel time and intensity of the ultrasonic guided wave signal and a position of the scattering group when judging that the excitation magneto-acoustic transducer and the omni-directionally receiving magneto-acoustic transducers form a scattering group; and determining the position of the scattering point as an effective scattering point when judging that the position of the scattering point is within a preset scattering region; finally performing curve fitting on all effective scattering points acquired to obtain a defect profile image of the metal plate to be detected after all of the N omni-directional magneto-acoustic transducers have excited omni-directional ultrasonic guided waves, it is possible to perform profile imaging on actually complex defects of the metal plate with high precision and high efficiency under convenient operations, and to accurately solve the position of the scattering point with fast calculation speed.

Figure 4:
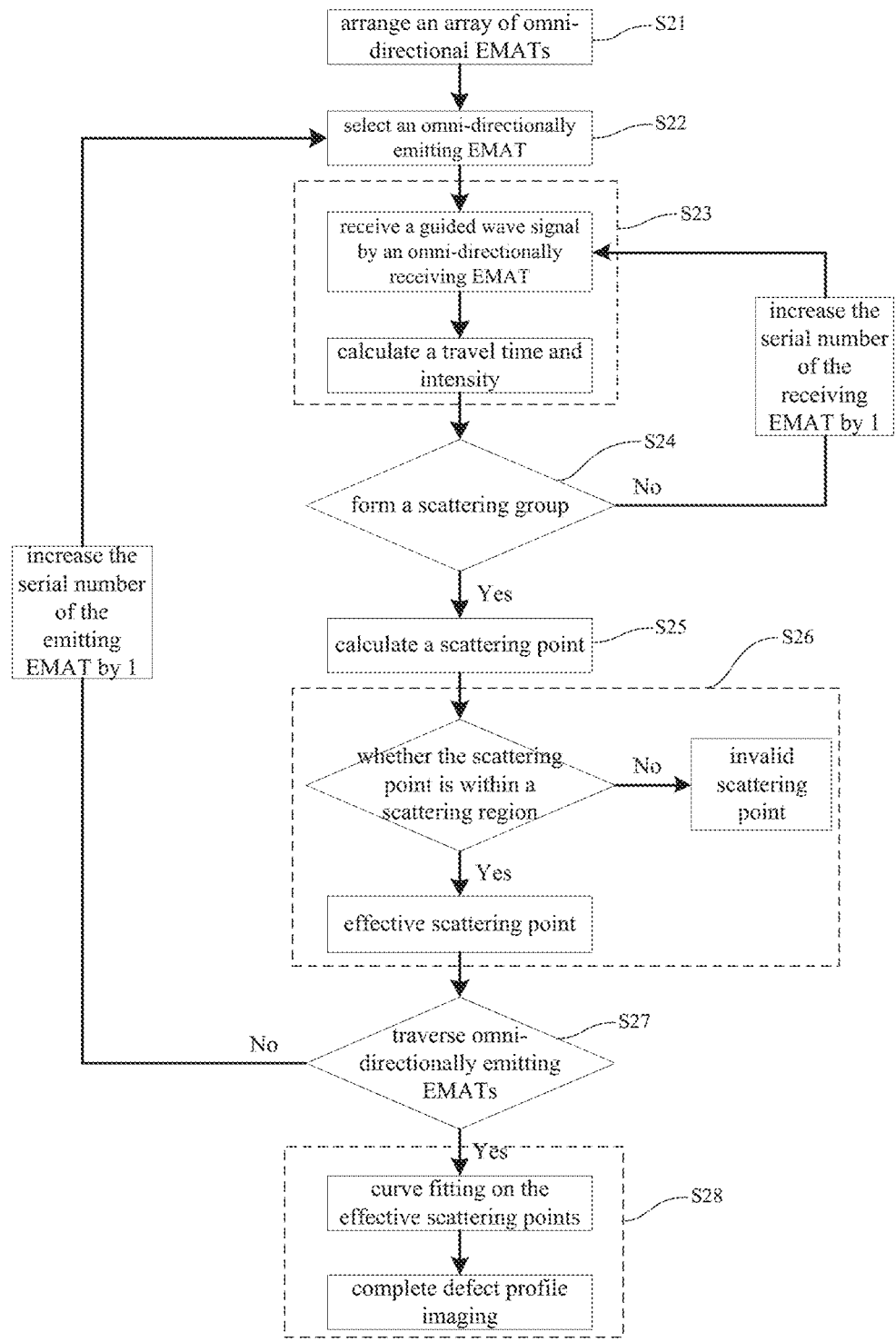
FIG. 4 is a flow chart of an imaging method based on guided wave scattering of omni-directional magneto-acoustic transducers according to another embodiment of the present disclosure.

FIG. 4 is a flow chart of an imaging method based on guided wave scattering of omni-directional magneto-acoustic transducers according to another embodiment of the present disclosure.

S21: 20 omni-directional magneto-acoustic transducers (EMATs) are uniformly arranged in a circular array around a detection region of a steel plate to be detected. The thickness of the steel plate is 3 mm, the diameter of the omni-directionally emitting/receiving magneto-acoustic transducer is 35 mm, and the diameter of the circular magneto-acoustic array is 66 cm.

S22: An $n^{th}$ omni-directional magneto-acoustic transducer is selected as an excitation magneto-acoustic transducer $T_n$ in this detection and excites omni-directional ultrasonic guided waves in the metal plate, where n=1, 2, . . . , 20.

S23: The omni-directional magneto-acoustic transducers receive ultrasonic guided wave signals in the metal plate. Assume that a total of M omni-directionally receiving magneto-acoustic transducers omni-directionally receive the ultrasonic guided wave signals (herein the specific value of M is not indicated, because the value of M is different when the detection is performed by different omni-directionally emitting EMAT), expressed as $R_m$, where m=1, 2, . . . , M; a travel time and intensity of each of guided wave detection signals received by the omni-directionally receiving EMATs are calculated, the data of the guided wave detection signals may be expressed as x (l), where l=1, 2, . . . , L, L is the total data points of the data of the guided wave detection signals (6500 for this embodiment), the signal intensity $A_R$ of the received guided wave detection signal is:

$$A_R = \frac{1}{L} \sum_{l=1}^{L} |x(l)|^2.$$

S24: it is judged whether the omni-directionally receiving magneto-acoustic transducer ($R_m$) by which the ultrasonic guided wave signal is received and the excitation magneto-acoustic transducers (omni-directionally emitting magneto-acoustic transducers) ($T_n$) by which the omni-directional guided wave is excited at this time form a scattering group using the travel time of the ultrasonic guided wave signal. For a certain ultrasonic guided wave detection signal received by the omni-directionally receiving magneto-acoustic transducer, an actually measured travel time thereof is $t_r$, a propagation velocity of the ultrasonic guided wave signal in the metal plate is v=3200 m/s, a planar rectangular coordinate system is established, a position of the excitation magneto-acoustic transducer is T, a position of the omni-directionally receiving magneto-acoustic transducer is R, and a theoretical time $t_s$ for which the ultrasonic guided wave signal directly propagates from the position T to the position R along a straight line is:

$$t_s = \frac{|\vec{TR}|}{v},$$

where $|\overrightarrow{TR}|$ is a vector length from the position T to the position R in the planar rectangular coordinate system.

If $t_r > t_s$, $R_m$ and $T_n$ form a scattering group for this ultrasonic guided wave signal; otherwise, $R_m$ and $T_n$ do not form a scattering group for this ultrasonic guided wave signal.

Whether the $R_m$ in Step 23 and the $T_n$ in Step 22 form a scattering group is judged one by one, if yes, performing S25; if no, turning to $R_{m+1}$ omni-directionally receiving magneto-acoustic transducer and returning to S23.

S25: For the scattering group $(T_n, R_m)$, a position P of a scattering point is solved using the position relation of $T_n$ and $R_m$, the intensity of the guided wave signal and the travel time $t_r$ of the received guided wave signal. In the planar rectangular coordinate system, the position P of the scattering point may be determined by solving the length $\|\overrightarrow{TP}\|$ of the vector $\overrightarrow{TP}$ and the length $|\overrightarrow{PR}|$ of the vector $\overrightarrow{PR}$. The position P of the scattering point may be calculated according to the travel time of the ultrasonic guided wave signal and a attenuation relationship of signal intensities during propagation and scattering of the ultrasonic guided wave signal, and formulas for calculating the position of the scattering group are:

$$|\overrightarrow{TP}| + |\overrightarrow{PR}| = v * t_r; \text{ and}$$

$$A * \frac{1}{\sqrt{|\overrightarrow{TP}|}} * a_s * \frac{1}{\sqrt{|\overrightarrow{PR}|}} = A_{RS},$$

where A is a signal intensity of the guided wave excited at the position T of the excitation magneto-acoustic transducer, $\alpha_s$ is a scattering attenuation coefficient of the signal intensity of the guided wave signal when the guided wave signal is scattered; and $A_{RS}$ is a signal intensity of a scattered wave received at the position R of the omni-directionally receiving magneto-acoustic transducer.

A method for solving the intensity A of the guided wave signal excited at the position T of the excitation magneto-acoustic transducer is $$A * \frac{1}{\sqrt{|\overrightarrow{TR}|}} = A_{RD},$$

where $A_{RD}$ is a signal intensity of a direct-wave received at the position R of the omni-directionally receiving magneto-acoustic transducer. The scattering attenuation coefficient $\alpha_s$ of the signal intensity when the guided wave is scattered is solved according to a relationship between a signal intensity $A_{Ri}$ of a non-scattered wave received by the omni-directionally receiving magneto-acoustic transducer and a theoretical attenuation amplitude $A_{Thi}$ of the excited guided wave signal. A method for solving the theoretical attenuation amplitude $A_{Thi}$ of the excited guided wave signal is $$A_{Thi} = A * \frac{1}{\sqrt{|\overrightarrow{TR_i}|}}$$

A transmission intensity comparison threshold $A_{Hi}$ of the guided wave is solved according to the theoretical attenuation amplitude $A_{Thi}$ of the excited guided wave signal: $A_{Hi} \in N_\delta(\beta * A_{Thi}) = (\beta * A_{Thi} - \delta, \beta * A_{Thi} + \delta)$, where $\beta$ is the simulation transmission coefficient of the guided wave, and is taken as 0.85 in the present embodiment, and $N_\delta(\beta * A_{Thi})$ is a neighborhood centered as $\beta * A_{Thi}$ and with a radius of $\delta$.

A method for solving the scattering attenuation coefficient of the signal intensity when the ultrasonic guided wave is scattered is:

$$a_s = 1 - \frac{1}{K}\sum_{i=1}^{K}\frac{A_{Ri}}{A_{Thi}},$$

where the number K is solved according to the following formula:

$$K = \text{Count}(i) s.t. (A_{Ri} < A_{Hi}),$$

where Count (i) is a function for counting i.

S26: The scattering region is solved to be a sector $R_1 TR_K$ according to the solved K positions Ri of the omni-directionally receiving magneto-acoustic transducers and the position T of the excitation magneto-acoustic transducer, it is judged whether the scattering point solved in S25 is within this sector region, if yes, the scattering point is an effective scattering point and S27 is performed, and if no, the scattering point is an invalid scattering point and is removed from a set of solved results of the scattering points.

S27: it is judging whether all the omni-directional magneto-acoustic transducers have excited the omni-directional ultrasonic guided waves in the metal plate, if yes, performing S28, and if no, selecting an $(n+1)^{th}$ omni-directional magneto-acoustic transducer as the excitation magneto-acoustic transducer $T_{n+1}$, and returning to S22. S28: A curve fitting is performed on all the obtained effective scattering points in directions of the respective scattering sides, 52 scattering points are obtained in total. In the planar rectangular coordinate system, a position of a $j^{th}$ scattering point is $P_j(x_j, y_j)$, where $j=1, 2, \ldots, 52$. The fitting curve D(x) for the scattering points is:

$$D(x) = \arg\min\sum_{j=1}^{S}|\phi(x_j) - y_j|^2 \text{ s.t. } \frac{d\phi}{dx}|_{P_j} = \frac{dy}{dx}|_{P_j}).$$

In addition, other configurations and effects of the imaging method based on guided wave scattering of omni-directional magneto-acoustic transducers according to an embodiment of the present disclosure are known to those skilled in the art, which will not be elaborated herein.

In summary, with the imaging method based on guided wave scattering of omni-directional magneto-acoustic transducers according to an embodiment of the present disclosure, by uniformly arranging the omni-directional magneto-acoustic transducers EMATs around the detection region in a circular array, using the travel time and intensity of each guided wave signal, and the position relationship of the corresponding scattering group, a model and method are established for solving the position of the scattering point in high-precision, effective scattering points are sieved out, the curve fitting is performed on all of the effective scattering points to establish a clear profile image of the actually complex defects, and the calculation is accurate, efficient and rapid, thus solving the following problems: the imaging precision of the actually complex defects of the metal plate detected with magneto-acoustic ultrasonic guided wave is low, the characteristic of the defect is difficult to extract, and a model for re-establishing the defect profile with the omni-directional transducer is difficult to solve.

In order to achieve the above-described embodiments, an imaging device based on guided wave scattering of omni-directional magneto-acoustic transducers is also provided in embodiments of the present disclosure.

Figure 5:
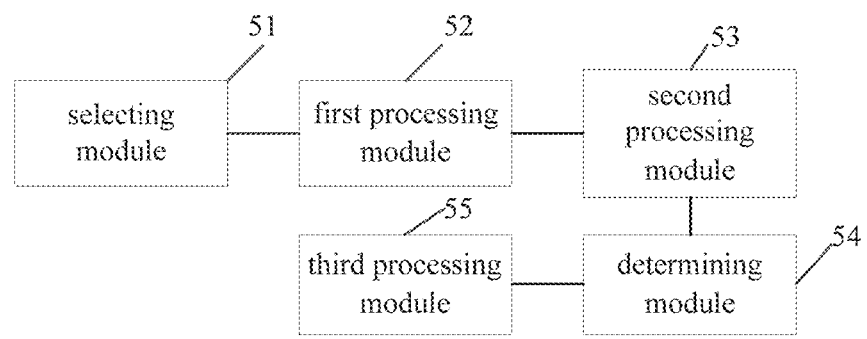
FIG. 5 is a schematic structural diagram of an imaging device based on guided wave scattering of omni-directional magneto-acoustic transducers according to an embodiment of the present disclosure.

FIG. 5 is a schematic structural diagram of an imaging device based on guided wave scattering of omni-directional magneto-acoustic transducers according to an embodiment of the present disclosure.

As shown in FIG. 5, the device includes a selecting module 51, a first processing module 52, a second processing module 53, a determining module 54, and a third processing module 55.

The selecting module 51 is configured to select an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave, where N is a positive integer.

The first processing module 52 is configured to select m omni-directional magneto-acoustic transducers from the N omni-directional magneto-acoustic transducers as omni-directionally receiving magneto-acoustic transducers to omni-directionally receive an ultrasonic guided wave signal, and configured to calculate a travel time and intensity of the ultrasonic guided wave signal, where m is a positive integer less than or equal to N.

The second processing module 53 is configured to judge whether the excitation magneto-acoustic transducer and the omni-directionally receiving magneto-acoustic transducers form a scattering group, if yes, to calculate a position of a scattering point according to the travel time and intensity of the ultrasonic guided wave signal, and a position of the scattering group.

The determining module 54 is configured to judge whether the position of the scattering point is within a preset scattering region, if yes, to determine the position of the scattering point as an effective scattering point.

The third processing module 55 is configured to allow the selecting module, the first processing module, the second processing module and the determining module to repeat their corresponding operations until all of the N omni-directional magneto-acoustic transducers have excited omni-directional ultrasonic guided waves, and configured to perform curve fitting on all effective scattering points acquired so as to obtain a defect profile image of the metal plate to be detected.

In an embodiment of the present disclosure, a formula for calculating the intensity $A_R$ of the ultrasonic guided wave signal is:

$$A_R = \frac{1}{L}\sum_{l=1}^{L} |x(l)|^2$$

where x(l) is the ultrasonic guided wave signal, where l=1, 2, ..., L, and L is a total number of data points of the ultrasonic guided wave signals.

In an embodiment of the present disclosure, judging whether the excitation magneto-acoustic transducer and the omni-directionally receiving magneto-acoustic transducers form a scattering group by the second processing module 53 includes: establishing a planar rectangular coordinate system; determining whether $t_r > t_s$, where $t_r$ is the travel time of the ultrasonic guided wave signal, $t_s$ is a theoretical time for which the ultrasonic guided wave signal propagates from a position T of the excitation magneto-acoustic transducer to a position R of the omni-directionally receiving magneto-acoustic transducer along a straight line and is determined according to $$t_s = \frac{|\overrightarrow{TR}|}{v},$$

where v is a propagation velocity of the ultrasonic guided wave signal, and $|\overrightarrow{TR}|$ is a vector length from the position T to the position R in the planar rectangular coordinate system; and if $t_r > t_s$, determining that the excitation magneto-acoustic transducer and the omni-directionally receiving magneto-acoustic transducers form the scattering group.

In an embodiment of the present disclosure, formulas for calculating the position of the scattering point according to the travel time and intensity of the ultrasonic guided wave signal, and the position of the scattering group are:

$$|\overrightarrow{TP}| + |\overrightarrow{PR}| = v*t_r; \text{ and}$$

$$A*\frac{1}{\sqrt{|\overrightarrow{TP}|}}*a_s*\frac{1}{\sqrt{|\overrightarrow{PR}|}} = A_{RS},$$

where T is a position of the excitation magneto-acoustic transducer, R is a position of the omni-directionally receiving magneto-acoustic transducer, P is the position of the scattering point, $|\overrightarrow{TP}|$ is a vector length from the position T to the position P in a planar rectangular coordinate system, $|\overrightarrow{PR}|$ is a vector length from the position P to the position R in the planar rectangular coordinate system. $A_{RS}$ is a signal intensity of a scattered wave received at the position R, A is a signal intensity of the omni-directional ultrasonic guided wave, $\alpha_s$ is a scattering attenuation coefficient of the intensity of the ultrasonic guided wave signal when the ultrasonic guided wave signal is scattered; and $$A*\frac{1}{\sqrt{|\overrightarrow{TR}|}} = A_{RD},$$

where $A_{RD}$ is a signal intensity of a direct-wave received at the position R.

In an embodiment of the present disclosure, judging whether the position of the scattering point is within a preset scattering region by the determining module 54 includes: acquiring a theoretical attenuation amplitude $$A_{Thi} = A*\frac{1}{\sqrt{|\overrightarrow{TR_i}|}}$$

of the omni-directional ultrasonic guided wave; calculating a transmission intensity comparison threshold $A_{Hi} \in N_\delta (\beta^* A_{Thi}) = (\beta^* A_{Thi} - \delta, \beta^* A_{Thi} + \delta)$ of the guided wave according to the theoretical attenuation amplitude of the omni-directional ultrasonic guided wave, where $\beta$ is a simulation transmission coefficient of the guided wave, $N_\delta(\beta^* A_{Thi})$ is a neighborhood centered as $\beta^* A_{Thi}$ and with a radius of $\delta$; acquiring a scattering attenuation coefficient $$a_s = 1 - \frac{1}{K}\sum_{i=1}^{K} \frac{A_{Ri}}{A_{Thi}}$$

of the intensity of the ultrasonic guided wave signal when the ultrasonic guided wave signal is scattered, where a calculating number K is K=Count(i) s.t. $(A_{Ri} < A_{Hi})$, where Count (i) is a function for counting i; obtaining the preset scattering region according to K positions of the omni-directionally receiving magneto-acoustic transducers and a position of the excitation magneto-acoustic transducer, and judging whether the position of the scattering point is within the preset scattering region.

In an embodiment of the present disclosure, a formula for the curve fitting is:

$$D(x) = \arg\left(\min \sum_{j=1}^{S} |\phi(x_j) - y_j|^2 \text{ s.t. } \left.\frac{d\phi}{dx}\right|_{P_j} = \left.\frac{dy}{dx}\right|_{P_j}\right)$$

where S is a total number of the effective scattering points, S is a positive integer, and a position of a $j^{th}$ scattering point is $P_j(x_j, y_j)$ in a planar rectangular coordinate system, where j=1, 2 . . . . , S.

It should be noted that the foregoing explanations for the imaging method based on guided wave scattering of omni-directional magneto-acoustic transducers according to the embodiments of the present disclosure are also applicable to the imaging device based on guided wave scattering of omni-directional magneto-acoustic transducers according to embodiments of the present disclosure, which will not be elaborated herein.

In summary, with the imaging device based on guided wave scattering of omni-directional magneto-acoustic transducers according to embodiments of the present disclosure, by selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave and selecting m omni-directional magneto-acoustic transducers as omni-directionally receiving magneto-acoustic transducers to omni-directionally receive an ultrasonic guided wave signal; further calculating a position of a scattering point according to the travel time and intensity of the ultrasonic guided wave signal and a position of the scattering group when judging that the excitation magneto-acoustic transducer and the omni-directionally receiving magneto-acoustic transducers form a scattering group; and determining the position of the scattering point as an effective scattering point when judging that the position of the scattering point is within a preset scattering region; finally performing curve fitting on all effective scattering points acquired to obtain a defect profile image of the metal plate to be detected after all of the N omni-directional magneto-acoustic transducers have excited omni-directional ultrasonic guided waves, it is possible to perform profile imaging on actually complex defects of the metal plate with high precision and high efficiency under convenient operations, and to accurately solve the position of the scattering point with fast calculation speed.

According to an embodiment of the present disclosure, there is provided an imaging device based on guided wave scattering of omni-directional magneto-acoustic transducers, including: a processor; and a memory for storing instructions executable by the processor, in which the processor is configured to perform the imaging method based on guided wave scattering of omni-directional magneto-acoustic transducers according to the above-mentioned embodiments of the present disclosure.

According to an embodiment of the present disclosure, there is provided a non-transitory computer-readable storage medium having stored therein instructions that, when executed by a processor of a mobile terminal, causes the mobile terminal to perform the imaging method based on guided wave scattering of omni-directional magneto-acoustic transducers according to the above-mentioned of the first aspect of the present disclosure.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment". "in another example," "in an example," "in a specific example," or "In an embodiment," in various places throughout this specification are not necessarily referring to the same embodiment or example of the present disclosure. Furthermore, the particular features, structures, materials, or characteristics may be combined in any suitable manner in one or more embodiments or examples.

In addition, terms such as "first" and "second" are used herein for purposes of description and are not intended to indicate or imply relative importance or significance. Thus, the feature defined with "first" and "second" may comprise one or more this feature. In the description of the present disclosure, "a plurality of" means two or more than two, unless specified otherwise.

It will be understood that, the flow chart or any process or method described herein in other manners may represent a module, segment, or portion of code that comprises one or more executable instructions to implement the specified logic function(s) or that comprises one or more executable instructions of the steps of the progress. Moreover, advantageous embodiments of the present disclosure comprises other implementations in which the order of execution is different from that which is depicted or discussed, including executing functions in a substantially simultaneous manner or in an opposite order according to the related functions. These and other aspects should be understood by those skilled in the art.

It can be understood that all or part of the steps in the method of the above embodiments can be implemented by instructing related hardware via programs, the program may be stored in a computer readable storage medium, and the program includes one step or combinations of the steps of the method when the program is executed.

In addition, each functional unit in the present disclosure may be integrated in one processing module, or each functional unit exists as an independent unit, or two or more functional units may be integrated in one module. The integrated module can be embodied in hardware, or software. If the integrated module is embodied in software and sold or used as an independent product, it can be stored in the computer readable storage medium.

The above mentioned storage medium may be read-only memories, magnetic disks, or optical disks. Although explanatory embodiments of the present disclosure have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An imaging method based on guided wave scattering of omni-directional magneto-acoustic transducers, comprising:
   S1, selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave, where N is a positive integer;
   S2, selecting m omni-directional magneto-acoustic transducers from the N omni-directional magneto-acoustic transducers as omni-directionally receiving magneto-acoustic transducers to omni-directionally receive an ultrasonic guided wave signal, and calculating a travel time and intensity of the ultrasonic guided wave signal, where m is a positive integer less than or equal to N;
   S3, judging whether the excitation magneto-acoustic transducer and the omni-directionally receiving magneto-acoustic transducers form a scattering group, if yes, calculating a position of a scattering point according to the travel time and intensity of the ultrasonic guided wave signal, and a position of the scattering group;
   S4, judging whether the position of the scattering point is within a preset scattering region, if yes, determining the position of the scattering point as an effective scattering point; and
   S5, repeating the steps S1 to S4 until all of the N omni-directional magneto-acoustic transducers have excited omni-directional ultrasonic guided waves, and performing curve fitting on all effective scattering points acquired to obtain a defect profile image of the metal plate to be detected.

2. The method of claim 1, wherein a formula for calculating the intensity $A_R$ of the ultrasonic guided wave signal is:

$$A_R = \frac{1}{L}\sum_{l=1}^{L}|x(l)|^2$$

where x(l) is the ultrasonic guided wave signal, where l=1, 2, ..., L, and L is a total number of data points of the ultrasonic guided wave signals.

3. The method of claim 1, wherein judging whether the excitation magneto-acoustic transducer and the omni-directionally receiving magneto-acoustic transducers form a scattering group comprises:
   establishing a planar rectangular coordinate system;
   determining whether $t_r > t_s$, where $t_r$ is the travel time of the ultrasonic guided wave signal, $t_s$ is a theoretical time for which the ultrasonic guided wave signal propagates from a position T of the excitation magneto-acoustic transducer to a position R of the omni-directionally receiving magneto-acoustic transducer along a straight line and is determined according to $$t_s = \frac{|\overrightarrow{TR}|}{v},$$

where v is a propagation velocity of the ultrasonic guided wave signal, and $|\overrightarrow{TR}|$ is a vector length from the position T to the position R in the planar rectangular coordinate system; and
   if $t_r > t_s$, determining that the excitation magneto-acoustic transducer and the omni-directionally receiving magneto-acoustic transducers form the scattering group.

4. The method of claim 1, wherein formulas for calculating the position of the scattering point according to the travel time and intensity of the ultrasonic guided wave signal, and the position of the scattering group are:

$$|\overrightarrow{TP}| + |\overrightarrow{PR}| = v * t_r; \text{ and}$$

$$A * \frac{1}{\sqrt{|\overrightarrow{TP}|}} * a_s * \frac{1}{\sqrt{|\overrightarrow{PR}|}} = A_{RS},$$

where T is a position of the excitation magneto-acoustic transducer, R is a position of the omni-directionally receiving magneto-acoustic transducers, P is the position of the scattering point, $|\overrightarrow{TP}|$ is a vector length from the position to the position P in a planar rectangular coordinate system, $|\overrightarrow{PR}|$ is a vector length from the position P to the position R in the planar rectangular coordinate system, $A_{RS}$ is a signal intensity of a scattered wave received at the position R, A is a signal intensity of the omni-directional ultrasonic guided wave, $\alpha_s$ is a scattering attenuation coefficient of the intensity of the ultrasonic guided wave signal when the ultrasonic guided wave signal is scattered; and $$A * \frac{1}{\sqrt{|\overrightarrow{TR}|}} = A_{RD},$$

where $A_{RD}$ is a signal intensity of a direct-wave received at the position R.

5. The method of claim 1, wherein judging whether the position of the scattering point is within a preset scattering region comprises:
   acquiring a theoretical attenuation amplitude $$A_{Thi} = A * \frac{1}{\sqrt{|\overrightarrow{TR_i}|}}$$

of the omni-directional ultrasonic guided wave;
   calculating a transmission intensity comparison threshold $A_{Hi} \in N_\delta(\beta * A_{Thi}) = (\beta * A_{Thi} - \delta, \beta * A_{Thi} + \delta)$ of the guided wave according to the theoretical attenuation amplitude of the omni-directional ultrasonic guided wave, where β is a simulation transmission coefficient of the guided wave, $N_\delta(\beta*A_{Thi})$ is a neighborhood centered as $\beta*A_{Thi}$ and with a radius of δ;

acquiring a scattering attenuation coefficient $$a_s = 1 - \frac{1}{K}\sum_{i=1}^{K}\frac{A_{Ri}}{A_{Thi}}$$

of the intensity of the ultrasonic guided wave signal when the ultrasonic guided wave signal is scattered, where a calculating number K is K=Count(i) s.t. ($A_{Ri}<A_{Hi}$), where Count (i) is a function for counting i; and obtaining the preset scattering region according to K positions of the omni-directionally receiving magneto-acoustic transducers and a position of the excitation magneto-acoustic transducer, and judging whether the position of the scattering point is within the preset scattering region.

6. The method of claim 1, wherein a formula for the curve fitting is:

$$D(x) = \arg\left(\min\sum_{j=1}^{S}|\phi(x_j) - y_j|^2 \text{ s.t. } \frac{d\phi}{dx}\bigg|_{P_j} = \frac{dy}{dx}\bigg|_{P_j}\right)$$

where S is a total number of the effective scattering points, S is a positive integer, and a position of a $j^{th}$ scattering point is $P_j(x_j, y_j)$ in a planar rectangular coordinate system, where j=1, 2, . . . , S.

7. An imaging device based on guided wave scattering of omni-directional magneto-acoustic transducers, comprising:
a processor; and
a memory for storing instructions executable by the processor,
wherein the processor is configured to perform an imaging method based on guided wave scattering of omni-directional magneto-acoustic transducers, the method comprising:
S1, selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave, where N is a positive integer;
S2, selecting m omni-directional magneto-acoustic transducers from the N omni-directional magneto-acoustic transducers as omni-directionally receiving magneto-acoustic transducers to omni-directionally receive an ultrasonic guided wave signal, and calculating a travel time and intensity of the ultrasonic guided wave signal, where m is a positive integer less than or equal to N;
S3, judging whether the excitation magneto-acoustic transducer and the omni-directionally receiving magneto-acoustic transducers form a scattering group, if yes, calculating a position of a scattering point according to the travel time and intensity of the ultrasonic guided wave signal, and a position of the scattering group;
S4, judging whether the position of the scattering point is within a preset scattering region, if yes, determining the position of the scattering point as an effective scattering point; and S5, repeating the steps S1 to S4 until all of the N omni-directional magneto-acoustic transducers have excited omni-directional ultrasonic guided waves, and performing curve fitting on all effective scattering points acquired to obtain a defect profile image of the metal plate to be detected.

8. The device of claim 7, wherein a formula for calculating the intensity $A_R$ of the ultrasonic guided wave signal is:

$$A_R = \frac{1}{L}\sum_{l=1}^{L}|x(l)|^2$$

where x(l) is the ultrasonic guided wave signal, where l=1, 2, . . . , L, and L is a total number of data points of the ultrasonic guided wave signals.

9. The device of claim 7, wherein judging whether the excitation magneto-acoustic transducer and the omni-directionally receiving magneto-acoustic transducers form a scattering group comprises:
establishing a planar rectangular coordinate system;
determining whether $t_r>t_s$, where $t_r$ is the travel time of the ultrasonic guided wave signal, $t_s$ is a theoretical time for which the ultrasonic guided wave signal propagates from a position T of the excitation magneto-acoustic transducer to a position R of the omni-directionally receiving magneto-acoustic transducer along a straight line and is determined according to $$t_s = \frac{|\overrightarrow{TR}|}{v},$$

where v is a propagation velocity of the ultrasonic guided wave signal, and $|\overrightarrow{TR}|$ is a vector length from the position T to the position R in the planar rectangular coordinate system; and
if $t_r>t_s$, determining that the excitation magneto-acoustic transducer and the omni-directionally receiving magneto-acoustic transducers form the scattering group.

10. The device of claim 7, wherein formulas for calculating the position of the scattering point according to the travel time and intensity of the ultrasonic guided wave signal, and the position of the scattering group are:

$$|\overrightarrow{TP}| + |\overrightarrow{PR}| = v*t_r; \text{ and}$$

$$A*\frac{1}{\sqrt{|\overrightarrow{TP}|}}*a_s*\frac{1}{\sqrt{|\overrightarrow{PR}|}} = A_{RS},$$

where T is a position of the excitation magneto-acoustic transducer, R is a position of the omni-directionally receiving magneto-acoustic transducers, P is the position of the scattering point, $|\overrightarrow{TP}|$ is a vector length from the position T to the position P in a planar rectangular coordinate system, $|\overrightarrow{PR}|$ is a vector length from the position P to the position R in the planar rectangular coordinate system, $A_{RS}$ is a signal intensity of a scattered wave received at the position R, A is a signal intensity of the omni-directional ultrasonic guided wave, $\alpha_s$ is a scattering attenuation coefficient of the intensity of the ultrasonic guided wave signal when the ultrasonic guided wave signal is scattered; and $$A * \frac{1}{\sqrt{|TR|}} = A_{RD},$$

where $A_{RD}$ is a signal intensity of a direct-wave received at the position R.

11. The device of claim 7, wherein judging whether the position of the scattering point is within a preset scattering region comprises:

acquiring a theoretical attenuation amplitude $$A_{Thi} = A * \frac{1}{\sqrt{|TR_i'|}}$$

of the omni-directional ultrasonic guided wave;

calculating a transmission intensity comparison threshold $A_{Hi} \in N_\delta(\beta*A_{Thi}) = (\beta*A_{Thi}-\delta, \beta*A_{Thi}+\delta)$ of the guided wave according to the theoretical attenuation amplitude of the omni-directional ultrasonic guided wave, where $\beta$ is a simulation transmission coefficient of the guided wave, $N_\delta(\beta*A_{Thi})$ is a neighborhood centered as $\beta*A_{Thi}$ and with a radius of $\delta$;

acquiring a scattering attenuation coefficient $$a_s = 1 - \frac{1}{K}\sum_{i=1}^{K} \frac{A_{Ri}}{A_{Thi}}$$

of the intensity of the ultrasonic guided wave signal when the ultrasonic guided wave signal is scattered, where a calculating number K is K=Count(i) s.t. $(A_{Ri} < A_{Hi})$, where Count (i) is a function for counting i; and obtaining the preset scattering region according to K positions of the omni-directionally receiving magneto-acoustic transducers and a position of the excitation magneto-acoustic transducer, and judging whether the position of the scattering point is within the preset scattering region.

12. The device of claim 7; wherein a formula for the curve fitting is:

$$D(x) = \arg\left(\min\sum_{j=1}^{S} |\phi(x_j) - y_j|^2 \text{ s.t. } \frac{d\phi}{dx}\bigg|_{P_j} = \frac{dy}{dx}\bigg|_{P_j}\right)$$

where S is a total number of the effective scattering points, S is a positive integer, and a position of a $j^{th}$ scattering point is $P_j(x_j, y_j)$ in a planar rectangular coordinate system, where j=1; 2, . . . , S.

13. A non-transitory computer-readable storage medium having stored therein instructions that, when executed by a processor of a mobile terminal, causes the mobile terminal to perform an imaging method based on guided wave scattering of omni-directional magneto-acoustic transducers, the method comprising:

S1, selecting an $n^{th}$ omni-directional magneto-acoustic transducer from N omni-directional magneto-acoustic transducers uniformly arranged in a detection region of a metal plate to be detected as an excitation magneto-acoustic transducer to excite an omni-directional ultrasonic guided wave, where N is a positive integer;

S2, selecting in omni-directional magneto-acoustic transducers from the N omni-directional magneto-acoustic transducers as omni-directionally receiving magneto-acoustic transducers to omni-directionally receive an ultrasonic guided wave signal, and calculating a travel time and intensity of the ultrasonic guided wave signal, where m is a positive integer less than or equal to N;

S3, judging whether the excitation magneto-acoustic transducer and the omni-directionally receiving magneto-acoustic transducers form a scattering group, if yes, calculating a position of a scattering point according to the travel time and intensity of the ultrasonic guided wave signal, and a position of the scattering group;

S4, judging whether the position of the scattering point is within a preset scattering region, if yes, determining the position of the scattering point as an effective scattering point; and S5, repeating the steps S1 to S4 until all of the N omni-directional magneto-acoustic transducers have excited omni-directional ultrasonic guided waves, and performing curve fitting on all effective scattering points acquired to obtain a defect profile image of the metal plate to be detected.

* * * * *